US008962866B2

(12) United States Patent
Amano et al.

(10) Patent No.: US 8,962,866 B2
(45) Date of Patent: Feb. 24, 2015

(54) SURFACE-MODIFIED SILICA POWDER AND METHOD FOR PRODUCING THE SAME, AS WELL AS TONER COMPOSITION FOR ELECTROPHOTOGRAPHY

(75) Inventors: Yuki Amano, Yokkaichi (JP); Naohiro Naito, Yokkaichi (JP); Hisao Okada, Yokohama (JP); Masaki Okubo, Tsukuba (JP); Yoshikazu Aoki, Tsukuba (JP); Hideyuki Otsuka, Koriyama (JP)

(73) Assignees: Nippon Aerosil Co., Ltd., Tokyo (JP); Hodogaya Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/980,203

(22) PCT Filed: Feb. 3, 2012

(86) PCT No.: PCT/JP2012/052445
§ 371 (c)(1), (2), (4) Date: Jul. 17, 2013

(87) PCT Pub. No.: WO2012/111452
PCT Pub. Date: Aug. 23, 2012

(65) Prior Publication Data

US 2013/0296578 A1 Nov. 7, 2013

(30) Foreign Application Priority Data

Feb. 17, 2011 (JP) ................................ 2011-031487

(51) Int. Cl.
*C01B 33/18* (2006.01)
*C07F 7/02* (2006.01)
*G03G 9/097* (2006.01)

(52) U.S. Cl.
CPC .............. *C07F 7/02* (2013.01); *G03G 9/09716* (2013.01); *G03G 9/09725* (2013.01); *C01B 33/18* (2013.01)
USPC .......................................... 549/214; 556/437

(58) Field of Classification Search
None
See application file for complete search history.

(56) References Cited

U.S. PATENT DOCUMENTS 6,994,834 B1 2/2006 Shirono et al.
2009/0099282 A1 4/2009 Muller et al.

FOREIGN PATENT DOCUMENTS

| | | |
|---|---|---|
| CN | 101184803 | 5/2008 |
| CN | 101767789 | 7/2010 |
| JP | 2008-250359 | 10/2008 |
| JP | 2008-545606 | 12/2008 |
| JP | 2009-234875 | 10/2009 |
| JP | 2010-160375 | 7/2010 |
| WO | 01/21529 | 3/2001 |
| WO | 01-21529 | 3/2001 |

OTHER PUBLICATIONS

Office Action for Chinese Patent Application. No. 201280003719.X which is dated Aug. 19, 2014, along with and English language translation.
International Search Report for PCT/JP2012/052445, mailed on May 1, 2012.
International Preliminary Report on Patentability for PCT/JP2012/052445, mailed on May 1, 2012.
Front page of WO 2006/125736, published on Nov. 30, 2006.
Office Action issued with respect to KR Patent Application No. 10-2013-7009754 mailed Sep. 22, 2014; along with an English Translation thereof.
Japanese Office Action issued with respect to JP 2012-557883, mailed Aug. 19, 2014; along with an English Translation.

*Primary Examiner* — Sun Jae Yoo
(74) *Attorney, Agent, or Firm* — Greenblum & Bernstein, P.L.C.

(57) ABSTRACT

Provided by the present invention is a surface-modified silica powder, characterized in that the said powder is obtained by surface treatment of a silica powder with one or two or more of a compound (A) and with an aminosilane (B), wherein the fixing rate of the compound (A) and the aminosilane (B) is a total of 50% or more, the hydrophobic rate is 80% or more, and the triboelectrostatic charge amount is 200 μC/g or less in its absolute value. The surface-modified silica powder of the present invention can stabilize many properties including fluidity and electrostatic properties while can significantly reduce problems such as fogging and decrease in image quality without significantly deteriorating characteristics of a developing agent and so forth when this is used as an external additive.

11 Claims, No Drawings

SURFACE-MODIFIED SILICA POWDER AND METHOD FOR PRODUCING THE SAME, AS WELL AS TONER COMPOSITION FOR ELECTROPHOTOGRAPHY

TECHNICAL FIELD

The present invention relates to: a surface-modified silica powder to be added into a powder paint, an electrophotographic toner, and so forth, as an external additive to improve powder fluidity, prevent caking, control charged electricity, and the like; a method for producing the same; and an electrophotographic toner composition containing the said powder. In more detail, the present invention relates to: a surface-modified silica powder, which is excellent in stability of a triboelectrostatic charge amount under a high temperature and high humidity environment or a low temperature and low humidity environment, and which is low in releasing amount of a surface treating agent used for surface treatment thereof whereby preventing poor transcription, fouling a machine, and so forth during printing; a method for producing the same; and an electrophotographic toner composition containing the said powder.

BACKGROUND ART

In an electrophotographic method using an instrument such as a copying machine, a laser printer, and a plain-paper fax machine, printing is generally done via processes including: a charging process in which a photo-sensitive body is uniformly charged by using a charging equipment such as a charging roller; an exposure process in which a light is irradiated on the charged photo-sensitive body in accordance with a printed data thereby forming a static latent image; a development process in which the latent image is visualized by attaching a toner to the static latent image thus formed; a transcription process in which the toner attached to the latent image is transferred to a body to be printed such as a paper; and a fixing process in which the transferred toner is fixed by utilizing heat or the like.

In the printing method using an electrophotographic method like this, an image is formed by utilizing a static electricity which is generated by charging a toner frictionally; and thus, in order to obtain a high quality image and to increase a printing speed, not only the toner needs to be provided with a sufficient triboelectrostatic charge amount but also this triboelectrostatic charge amount provided to the toner needs to be stable. For this purpose, powders of a metal oxide such as silica, titania, and alumina have been conventionally added as an external additive to provide the toner with an intended charge amount, to stabilize the triboelectrostatic charge amount provided to the toner, to improve fluidity of the toner, and so forth. Especially, silica is used widely because silica having a very small particle diameter is available cheaply, excellent fluidity can be obtained when it is added to the toner, and charging amount thereof is so high that the toner can be provided with a sufficient charge.

However, a silica powder in itself is hydrophilic thereby easily influenced by a use environment such as temperature and humidity as well as by a printing environment; and thus, for example, there are such problems that the toner cannot be provided with sufficient fluidity under a high temperature and high humidity environment in which silica powders agglomerate, and that, under an environment in which a drastic humidity change takes place, a triboelectrostatic charge amount of the external additive itself is not stabilized thereby leading to insufficient charge control of the toner.

Because of this, for example, a silica powder whose surface is made hydrophobic by surface treatment is used as an external additive of a toner (for example, see Patent Document 1). In the invention according to Patent Document 1, a silane coupling agent and a silicone oil are used for surface treatment of a silica powder. As to the treating agent, use of a silicone varnish, a silylation agent, and the like are investigated.

On the other hand, if these treating agents used to afford the hydrophobicity are not attached or fixed adequately well to the powder surface, when this powder is added to a toner, a part thereof is readily released as passage of time or as the use frequency thereof increases. Because of this, in the powders having these treating agents insufficiently fixed thereto, the hydrophobic effect that is enhanced by the surface treatment decreases gradually; and as a result, resistance of the triboelectrostatic charge amount to humidity change decreases simultaneously. In addition, its fluidity-affording effect to the toner decreases too, thereby causing problems such as poor transcription in electrophotography, fouling of a machine, and so forth. To the problems like these, a toner which is added as the external additive with silica microparticles having a treating agent fixed thereto with the fixing rate of 30% or more by mass, or preferably 60% or more by mass, as the carbon base, is disclosed (for example, see Patent Document 2).

Patent Documents

Patent Document 1: Japanese Patent Application Laid-Open No. 2008-250359 (Claim 6, Claim 15, and paragraphs [0091] to [0095])

Patent Document 2: Japanese Patent Application Laid-Open No. 2010-160375 (Claim 1 and paragraphs [0020] and [0023])

DISCLOSURE OF INVENTION

Problems to be Solved by the Invention

However, although it is reported that the powder used in the invention of the foregoing Patent Document 2 has the fixing rate of 30% or more by mass or preferably 60% or more by mass, there is a problem of a large triboelectrostatic charge amount in its absolute value. For example, in the color toner in which carbon black cannot be added, usually there is a tendency that a triboelectrostatic charge amount of the toner becomes too large in its absolute value as compared with a black toner. Because of this, as to the external additive added to the color toner, an additive having a smaller triboelectrostatic charge amount in its absolute value as compared with the toner added to the black toner is desirable. On the other hand, in the powder used in the invention of Patent Document 2, the triboelectrostatic charge amount thereof is large in its absolute value because of properties of the used treating agent, and in addition, the triboelectrostatic charge amount itself becomes readily unstable.

Objects of the present invention are to provide: a surface-modified silica powder having, when added as an external additive to a toner, excellent temporal stability of the triboelectrostatic charge amount, which is stable not only under a low temperature and low humidity condition but also under a high temperature and high humidity condition, while suppressing such effects as poor transcription, fouling of a machine, and so forth during printing; a method for producing the same; and an electrophotographic toner composition which contains the said powder.

Means for Solving the Problems

A first aspect of the present invention relates to a surface-modified silica powder, characterized in that the surface of the silica powder is treated by using:

one or two or more of a compound (A) shown by any one of the following general formulae (1) to (4) as a first treating agent, and an aminosilane (B) as a second treating agent, respectively, wherein a fixing rate of the compound (A) and the aminosilane (B) is a total of 50% or more, a hydrophobic rate is 80% or more, and a triboelectrostatic charge amount is 200 μC/g or less in its absolute value.

[Chem. 1]

(1)

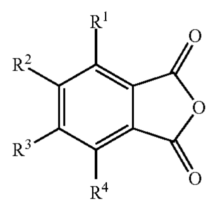

wherein $R^1$ to $R^4$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^1$ and $R^2$, $R^2$ and $R^3$, and $R^3$ and $R^4$ may be bonded with each other to form a ring by a single bond or via an optionally substituted methylene group, an oxygen atom, or a sulfur atom.

[Chem. 2]

(2)

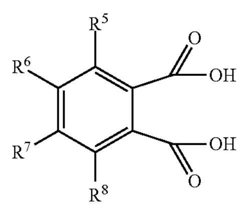

wherein $R^5$ to $R^8$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^5$ and $R^6$, $R^6$ and $R^7$, and $R^7$ and $R^9$ may be bonded with each other to form a ring by a single bond or via an optionally substituted methylene group, an oxygen atom, or a sulfur atom.

[Chem. 3]

(3)

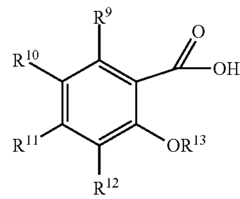

wherein $R^9$ to $R^{12}$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^9$ and $R^{10}$, $R^{10}$ and $R^{11}$, and $R^{11}$ and $R^{12}$ may be bonded with each other to form a ring by a single bond or via an optionally substituted methylene group, an oxygen atom, or a sulfur atom. $R^{13}$ represents a hydrogen atom, a deuterium atom, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted aromatic hydrocarbon group, an optionally substituted heterocyclic group, an optionally substituted condensed polycyclic aromatic group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group.

[Chem. 4]

(4)

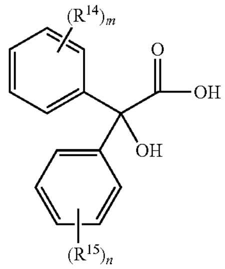

wherein $R^{14}$ and $R^{15}$ may be the same or different with each other while representing a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group, wherein these substituents may be bonded with each other to form a ring. Reference characters "m" and "n" may be the same or different with each other while representing zero or an integer of 1 to 4.

A second aspect of the present invention is based on the first aspect, characterized further in that the silica powder is a fumed silica.

A third aspect of the present invention is based on the first or the second aspect, characterized further in that the first treating agent is one or two or more of a compound (A) shown by the general formula (1) or (2), and the second treating agent is a primary aminosilane or a secondary aminosilane.

A fourth aspect of the present invention is based on the first to the third aspects, characterized further in that the first treating agent is one or two or more of a compound (A) shown by the general formula (1) or (2), wherein $R^1$ to $R^4$ in the general formula (1) represent a branched alkyl group having 4 to 6 carbon atoms or an optionally substituted aryl oxycarbonyl group, and $R^5$ to $R^8$ in the general formula (2) represent a branched alkyl group having 4 to 6 carbon atoms or an optionally substituted aryl oxycarbonyl group.

A fifth aspect of the present invention is based on the first to the fourth aspects, characterized further in that a molar ratio of the first treating agent to the second treating agent (first treating agent/second treating agent) used in the surface treatment is in the range of 0.2 to 1.5, and amount of the second treating agent used for the silica powder is in the range of 0.01 to 1.0 mg per 1 $m^2$ of the silica powder surface area.

A sixth aspect of the present invention is characterized further in that, in a method for producing a silica powder whose surface is modified by surface treatment of a silica powder, the said surface treatment is done by using a first treating agent and a second treating agent, wherein the first treating agent is one or two or more of a compound (A) shown by any one of the following general formulae (1) to (4), and the second treating agent is an aminosilane (B).

[Chem. 5]

(1)

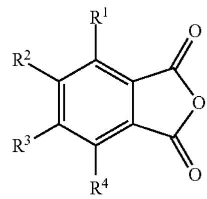

wherein $R^1$ to $R^4$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^1$, and $R^2$, $R^2$ and $R^3$, and $R^3$ and $R^4$ may be bonded with each other to form a ring by a single bond or via an optionally substituted methylene group, an oxygen atom, or a sulfur atom.

[Chem. 6]

(2)

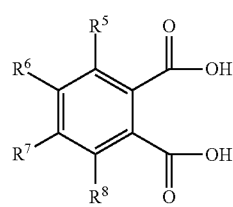

wherein $R^5$ to $R^8$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^5$ and $R^6$, $R^6$ and $R^7$, and $R^7$ and $R^8$ may be bonded with each other to form a ring by a single bond or via an optionally substituted methylene group, an oxygen atom, or a sulfur atom.

[Chem. 7]

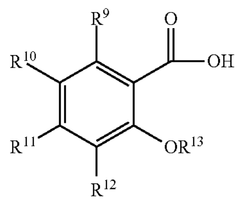

(3)

wherein $R^9$ to $R^{12}$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^9$ and $R^{10}$, $R^{10}$ and $R^{11}$, and $R^{11}$ and $R^{12}$ may be bonded with each other to form a ring by a single bond or via an optionally substituted methylene group, an oxygen atom, or a sulfur atom. $R^{13}$ represents a hydrogen atom, a deuterium atom, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted aromatic hydrocarbon group, an optionally substituted heterocyclic group, an optionally substituted condensed polycyclic aromatic group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group.

[Chem. 8]

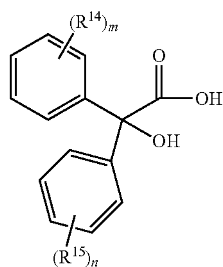

(4)

wherein $R^{14}$ and $R^{15}$ may be the same or different with each other while representing a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group, wherein these groups may be bonded with each other to form a ring. Reference characters "m" and "n" may be the same or different with each other while representing zero or an integer of 1 to 4.

A seventh aspect of the present invention is based on the sixth aspect, characterized further in that the second treating agent is added to and mixed with the silica powder, the resulting mixture is treated at the temperature of 120 to 300° C. and with the time for 10 to 300 minutes under an inert gas atmosphere, the first treating agent is added to and mixed with the silica powder having been treated with the second treating agent, and then, this mixture is treated at the temperature of 120 to 300° C. and with the time for 10 to 300 minutes under an inert gas atmosphere.

An eighth aspect of the present invention is based on the sixth aspect, characterized further in that after a third treating agent is prepared by mixing the first treating agent and the second treating agent, the said third treating agent is added to and mixed with the silica powder, and then, surface treatment thereof is carried out at the temperature of 120 to 300° C. and with the time for 10 to 300 minutes under an inert gas atmosphere.

A ninth aspect of the present invention is based on the sixth to the eighth aspects, characterized further in that a molar ratio of the first treating agent to the second treating agent (first treating agent/second treating agent) used in the surface treatment is in the range of 0.2 to 1.5, and amount of the second treating agent used for the silica powder is in the range of 0.01 to 1.0 mg per 1 $m^2$ of the silica powder surface area.

A tenth aspect of the present invention is a toner external additive comprising the surface-modified silica powder based on the first to the fifth aspects.

An eleventh aspect of the present invention is an electrophotographic toner composition which contains the toner external additive based on the tenth aspect.

Advantages

The surface-modified silica powder according to the first aspect of the present invention relates to the silica powder whose surface is treated by using one or two or more of a compound (A) shown by any one of the general formulae (1) to (4) as a first treating agent and an aminosilane (B) as a second treating agent, respectively, wherein the fixing rate of the compound (A) and the aminosilane (B) is a total of 50% or more, the hydrophobic rate is 80% or more, and the triboelectrostatic charge amount is 200 μC/g or less in its absolute value. In the surface-modified silica powder of the present invention, the surface treatment is done by using the above-mentioned two treating agents, so that these treating agents are fixed onto the powder surface with a high fixing rate. By so doing, the triboelectrostatic charge amount becomes small in its absolute value, the temporal stability of the triboelectrostatic charge amount becomes excellent, and the triboelectrostatic charge amount is stabilized in use not only under a low temperature and low humidity environment but also under a high temperature and high humidity environment. Therefore, when the surface-modified silica powder of the present invention is used as an external additive for a toner, influence from the use frequency and the use environment can be minimized, thereby leading to drastic reduction of a problem such as poor transcription and fouling of a machine during printing.

In the production method according to the sixth aspect of the present invention, the surface treatment is done by using a first treating agent and a second treating agent, wherein the first treating agent is one or two or more of a compound (A) shown by any one of the general formulae (1) to (4), and the second treating agent is an aminosilane (B). With this, the surface-modified silica powder having high hydrophobicity as well as high fixing rates of the treating agents, excellent temporal stability of the triboelectrostatic charge amount, and excellent stability under the use environment including temperature and humidity can be produced.

The electrophotographic toner composition according to the eleventh aspect of the present invention contains the surface-modified silica powder of the present invention as an external additive so that influence from the use frequency and the use environment can be minimized, thereby leading to drastic reduction of a problem such as poor transcription and fouling of a machine during printing.

MODES FOR CARRYING OUT THE INVENTION

Next, modes for carrying out the present invention will be explained.

The surface-modified silica powder of the present invention is a silica powder whose surface is modified by surface treatment thereof, that is, the powder whose surface is fixed with a compound (A) as a first treating agent and an aminosilane (B) as a second treating agent which are used during the time of surface treatment. The compound (A) used as the first treating agent is shown by the following general formulae (1) to (4); this compound has an excellent effect to enhance hydrophobicity of the silica powder, while its reactivity with the surface of the silica powder is low. Accordingly, it is difficult to fix the compound (A) onto surface of the silica powder with a high fixing rate when surface treatment is done by using only this treating agent; and thus, the effect to keep hydrophobicity during passage of time is so low that the stability in the triboelectrostatic charge amount is gradually lost under the use environment. On the other hand, the aminosilane (B) used as the second treating agent has a very high reactivity to surface of the silica powder as well as to the first treating agent; and on top of this, it has a characteristic to lower the triboelectrostatic charge amount of the silica powder.

In the surface-modified silica powder of the present invention, by using these two treating agents for surface treatment thereof, the compound (A) used as the first treating agent is fixed onto surface of the silica powder via the aminosilane (B) used as the second treating agent.

The aminosilane (B) is firmly fixed onto surface of the silica powder, for example, by a covalent bond formed by a dehydration condensation reaction of a silanol group which is formed by hydrolysis of an alkoxy group of the aminosilane (B) with a silanol group present before this treatment on surface of the silica powder. In addition, the compound (A) used as the first treating agent is firmly bonded by a covalent bond (amide bond) between a carboxyl group or a carboxylic acid anhydride group (—CO—O—CO—) of the compound (A) and an amino group of the aminosilane (B).

That is, by using both the compound (A) used as the first treating agent and the aminosilane (B) used as the second treating agent, the surface-modified silica powder of the present invention is fixed on its surface in a high fixing rate with surface treating agents that could not have been used suitably because of a fixing problem.

The fixing rate of the compound (A) and the aminosilane (B) reaches 50% or more, or even in the range of 70% to 100% (both ends inclusive) as a total of them. With this, temporal stability of the triboelectrostatic charge amount can be obtained. If the fixing rate is less than 50%, when this is added to a toner as an external additive, the treating agents are gradually released from surface of the powders thereby causing decrease in hydrophobicity so that the triboelectrostatic charge amount tends to be unstable during the passage of time. Because of this, effects to the triboelectrostatic charge amount of the toner increases thereby causing a problem such as poor transcription and fouling of a machine during printing as the use frequency increases. Meanwhile, the fixing rate of these treating agents means the fixing rate based on the carbon amount in the surface-modified silica powders. Specifically, this means the rate of the carbon amount remained on the powders after extraction treatment thereof by a Soxhlet extractor (manufactured by Buchi Labortechnik AG) under a specific condition as shown in the later-mentioned Example to the carbon amount before the extraction treatment.

In addition, the surface-modified silica powder of the present invention has the hydrophobicity rate of 80% or more. With this, the triboelectrostatic charge amount is stabilized in use under conditions of not only a low temperature and low humidity environment but also a high temperature and high humidity environment. The hydrophobicity rate shows the degree of hydrophobicity of the surface-modified silica powder. Specifically, the hydrophobicity rate is the transmittance measured by a colorimeter at 500 nm of the sample solution taken from the lower layer of a mixture solution of the powders with pure water obtained by shaking the mixture solution for 10 minutes followed by settling it for 10 minutes, as shown in the later-mentioned Example. If the hydrophobicity rate is less than 80%, there appear problems that the triboelectrostatic charge amount becomes unstable by change of a use environment such as temperature and humidity, its fluidity-affording effect to the toner is decreased, and agglomeration takes place readily.

Further, the surface-modified silica powder of the present invention has the triboelectrostatic charge amount of 200 μC/g or less in its absolute value. This is the triboelectrostatic charge amount after 5 minutes since the powders are dispersed in a ferrite carrier. The surface-modified silica powder of the present invention has very low triboelectrostatic charge amount in its absolute value because surface of the powder is treated with a compound (A) shown by the general formulae (1) to (4) and an aminosilane (B) as the surface treating agents. Because of this, even if this is used as an external additive to a color toner and so forth, triboelectrostatic charge amount of the toner can be suppressed so that it may not become excessively high; and thus, problems such as fogging and decrease in image quality during printing can be significantly reduced.

As to the compound (A) used as the first treating agent, compounds shown by any one of the following general formulae (1) to (4) may be mentioned.

[Chem. 9]

(1)

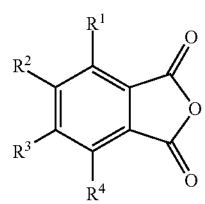

wherein $R^1$ to $R^4$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^1$ and $R^2$, $R^2$ and $R^3$, and $R^3$ and $R^4$ may be bonded with each other to form a ring by a single bond or via an optionally substituted methylene group, an oxygen atom, or a sulfur atom.

Specific example of the compound (A) shown by the general formula (1) includes 4-ter-butylphthalic anhydride, trimellitic anhydride, and trimellitic anhydride 4-tert-butylphenol ester.

[Chem. 10]

(2)

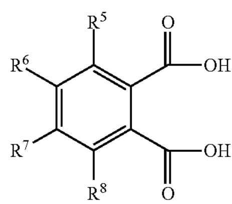

wherein $R^5$ to $R^8$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^5$ and $R^6$, $R^6$ and $R^7$, and $R^7$ and $R^8$ may be bonded with each other to form a ring by a single bond or via an optionally substituted methylene group, an oxygen atom, or a sulfur atom.

Specific example of the compound (A) shown by the general formula (2) includes phthalic acid, trimellitic acid, and 4-tert-butylphthalic acid.

[Chem. 11]

(3)

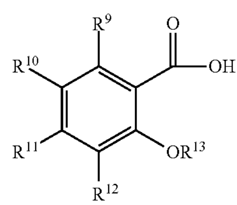

wherein $R^9$ to $R^{12}$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^9$ and $R^{10}$, $R^{10}$ and $R^{11}$, and $R^{11}$ and $R^{12}$ may be bonded with each other to form a ring by a single bond or via an optionally substituted methylene group, an oxygen atom, or a sulfur atom. $R^{13}$ represents a hydrogen atom, a deuterium atom, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted aromatic hydrocarbon group, an optionally substituted heterocyclic group, an optionally substituted condensed polycyclic aromatic group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group.

Specific example of the compound (A) shown by the general formula (3) includes 3,5-di(tert-butyl)salicylic acid, 3-phenylsalicylic acid, 4-(trifluoromethyl)salicylic acid, 2,4,6-trihydroxybenzoic acid, 2,3,4-trimethoxybenzoic acid, and 2-(2-hydroxy)benzoyloxy benzoic acid.

[Chem. 12]

(4)

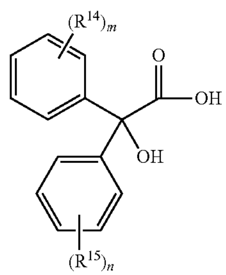

wherein $R^{14}$ and $R^{15}$ may be the same or different with each other while representing a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group, wherein these groups may be bonded with each other to form a ring. Reference characters "m" and "n" may be the same or different with each other while representing zero or an integer of 1 to 4.

Specific example of the compound (A) shown by the general formula (4) includes 2,2-diphenyl glycolic acid, 2-(4-tert-butyl)phenyl-2-phenyl glycolic acid, 2,2-bis{(4-tert-butyl)phenyl}glycolic acid, 2-(4-carboxylphenyl)-2-phenyl glycolic acid, and 2,2-bis{(4-carboxyl)phenyl}glycolic acid.

The reason why compounds (A) shown by the general formulae (1) to (4) are used as the first treating agent is because these compounds can enhance hydrophobicity of the silica powder significantly high. The other reason for this is because these compounds have a carboxyl group or a carboxylic acid anhydride group (—CO—O—CO—) which can form a strong covalent bond with the aminosilane (B) used as the second treating agent, whereby giving a high fixing rate.

These compounds (A) shown by the general formulae (1) to (4) may be used singly or as a mixture of two or more of them, while it is preferable to use one or two or more of the compound (A) shown by the general formula (1) or (2) in order to obtain a high fixing rate. In addition, of the compounds (A) shown by the general formula (1), a compound (A) having $R^1$ to $R^4$ of a branched alkyl group having 4 to 6 carbon atoms or an optionally substituted aryl oxycarbonyl group is preferable in order to enhance the hydrophobic rate of the powder and the temporal stability of the triboelectrostatic charge amount. Further, of the compounds (A) shown by the general formula (2), a compound (A) having $R^5$ to $R^8$ of a branched alkyl group having 4 to 6 carbon atoms or an optionally substituted aryl oxycarbonyl group is especially preferable in order to enhance the hydrophobic rate of the powder and the temporal stability of the triboelectrostatic charge amount.

On the other hand, the aminosilane (B) used as the second treating agent is not particularly restricted as far as the aminosilane itself can be bonded to surface of the silica powder, while at the same time it can fix the compound (A) used as the first treating agent to surface of the silica powder, and the triboelectrostatic charge amount of the powder can be made small in its absolute value. Specifically, an aminosilane having not only an amino group, which can form a covalent bond (amide bond) with a carboxyl group or a carboxylic acid anhydride group (—CO—O—CO—) of the compound (A), but also a group such as an alkoxy group and a chloro group which can readily form a covalent bond by a dehydration condensation reaction with a silanol group present on surface of the silica powder by hydrolysis is preferably used. Illustrative example of the aminosilane like this includes a primary aminosilane such as $(MeO)_3SiCH_2CH_2CH_2NH_2$, $(EtO)_3SiCH_2CH_2CH_2NH_2$, $(i\text{-}PrO)_3SiCH_2CH_2CH_2NH_2$, $(EtO)_3SiCH_2NH_2$, $Cl_3SiCH_2CH_2CH_2NH_2$, $(MeO)_2MeSiCH_2CH_2CH_2NH_2$, and $(EtO)_2MeSiCH_2CH_2CH_2NH_2$. Meanwhile, in these formulae, Me means a methyl group, Et means an ethyl group, and i-Pr means an isopropyl group. Of these, $(MeO)_3SiCH_2CH_2CH_2NH_2$ (γ-aminopropyl trimethoxy silane) and $(EtO)_3SiCH_2CH_2CH_2NH_2$ (γ-aminopropyl triethoxy silane) are particularly preferable.

In view of a high effect to minimize the triboelectrostatic charge amount of the powder in its absolute value, other than the foregoing aminosilanes, secondary aminosilanes such as $(MeO)_3SiCH_2CH_2CH_2NHEt$, $(MeO)_3SiCH_2CH_2CH_2NHBu$, $(MeO)_3SiCH_2CH_2CH_2NHC_6H_5$, $Cl_3SiCH_2CH_2CH_2NHEt$, $(AcO)_3SiCH_2CH_2CH_2NHEt$, and $(MeO)_3SiCH_2CH_2CH_2NHCH_2CH_2OMe$ are preferable. Meanwhile, in the above formulae, Me indicates a methyl group, Et indicates an ethyl group, and Ac indicates an acetyl group.

The raw material silica powder for the surface-modified silica powder of the present invention may be a so-called wet silica that is obtained by neutralization of an aqueous sodium silicate solution with an acid or an alkaline metal salt, though a so-called dry silica (fumed silica) that is obtained by a spray flame method in which a flame hydrolysis of a volatile silicon compound such as a silicon halide is carried out is preferable. This is because the dry silica has excellent characteristics in affording an intended charge to a toner, stabilizing the afforded triboelectrostatic charge amount, and improving fluidity of a toner.

The average diameter of primary particles of the raw material silica powder is preferably in the range of 5 to 120 nm, and the BET specific surface area thereof is preferably in the range of 10 to 400 $m^2/g$. If the BET specific surface area is less than this lower limit, the average particle diameter is too large so that production of the powder by a dry method becomes difficult. On the other hand, if the BET specific surface area is more than this upper limit, the average particle diameter is too small so that an industrial product thereof is not available under the current situation. Meanwhile, the average diameter of primary particles in the present specification is an average value of the measured particle diameters of 100 microparticles arbitrarily selected in the picture taken by a TEM (transmission electron microscope). The BET specific surface area is a value that is obtained by the BET method.

Next, a method for producing the surface-modified silica powder of the present invention will be explained.

Production Method According to a First Embodiment:

In the production method according to this first embodiment, the surface treatment is done by a two-stage process which involves a step of treating a silica power with a second treating agent, and then, a step of further treating the silica powder which has been treated with the second treating agent as mentioned above with a first treating agent.

Specifically, to begin with, an aminosilane (B) with the use amount thereof being preferably 0.01 to 1.0 mg given to per 1 $m^2$ of surface area of the raw material silica powder is arranged as the second treating agent. If the use amount of the second treating agent is less than this lower limit, sufficient effects by the surface treatment cannot be obtained, and on top of this, the first treating agent cannot be fixed onto the powder surface with a high fixing rate; and thus, below this range is not suitable. On the other hand, if the use amount thereof is above the upper limit, excess amount of the treating agent is released into a toner thereby tending to make the triboelectrostatic charge amount of the toner unstable; and thus, above this range is not suitable. In this range, the use amount of the second treating agent giving 0.03 to 0.5 mg onto per 1 $m^2$ of surface area of the silica powder is particularly preferable. The aminosilane (B) thus arranged may be used as it is; but in order to effect the surface treatment uniformly, it is preferable to use it as an aminosilane solution after it is diluted by or dissolved in an organic solvent. This organic solvent is not particularly restricted; and thus, various organic solvents such as ethanol and methanol may be used. Addition amount of the organic solvent to prepare the aminosilane solution is preferably in the range of 0 to 300 parts by mass, or more preferably 50 to 200 parts by mass, relative to 100 parts by mass of the aminosilane. Addition amount of the organic solvent more than 300 parts by mass is not suitable because the powders tend to agglomerate.

Then, the compound (A) having the mass ratio thereof to the second treating agent (first treating agent/second treating agent) adjusted preferably in the range of 0.2 to 1.5 is arranged as the first treating agent. If use amount of the first treating agent relative to the second treating agent is below this lower limit, sufficient effects by the surface treatment cannot be obtained. On the other hand, if the amount thereof is above this upper limit, excess amount of the treating agent is released into a toner thereby tending to make the triboelectrostatic charge amount of the toner unstable; and thus, above this range is not suitable. The compound (A) thus arranged is preferably used as a dissolved solution obtained by dissolving it into an organic solvent to effect the surface treatment uniformly. This organic solvent is not particularly restricted; and thus, various kind organic solvents such as ethanol and methanol may be used. Addition amount of the organic solvent to prepare the dissolved solution of the compound (A) is preferably in the range of 10 to 1000 parts by mass, or more preferably 300 to 700 parts by mass, relative to 100 parts by mass of the compound (A). If addition amount of the organic solvent is less than 10 parts by mass, the surface treatment tends to be ununiform, while if it is more than 1000 parts by mass, the powders tend to agglomerate; and thus, outside the above-mentioned range is not suitable.

Then, the silica powders to be surface-modified are taken into a reactor; and then, the above-prepared aminosilane solution and water are added to the powders while stirring the powders with a rotating blade and the like under an inert gas atmosphere such as a nitrogen gas. The reason why the inert gas such as a nitrogen gas is used is to prevent oxidation of the treating agent from occurring. The reason why water is added is to form a silanol group by reacting the aminosilane with water. Amount of water to be added in this reaction is preferably in the range of 0.1 to 5 parts by mass relative to 100 parts by mass of the silica powders. Thereafter, this mixture is mixed in the reactor at the temperature of 120 to 300° C. and with the time for 10 to 300 minutes. The reason why the temperature range of 120 to 300° C. is used is because below this lower limit the surface modification of the silica powders is insufficient so that sufficient effects by this surface treatment cannot be obtained. On the other hand, if it is above the upper limit, the surface treating agent decomposes in a certain instance; and thus, above this upper limit is not suitable. In the above-mentioned range, the temperature range of 150 to 250° C. in the treatment is particularly preferable. In addition, if the mixing time is shorter than the lower limit, similarly to the case of the temperature, sufficient effects by this surface treatment cannot be obtained. On the other hand, if the time is longer than the upper limit, problems such as agglomeration of the powders and decomposition of the treating agent take place; or the reaction does not proceed further even if the mixing time is prolonged beyond the upper limit so that it is not suitable from the economical view point. In this range, the mixing time of 20 to 120 minutes is particularly preferable. After the treatment, the powders are cooled by cooling water, by allowing to stand them at room temperature, or by other methods.

Subsequently to the surface treatment by the second treating agent, surface treatment is carried out by using the first treating agent. Firstly, the silica powders after the surface treatment by the second treating agent are cooled and then taken into a reactor; and then, similarly to before, the above-prepared dissolved solution of the compound (A) is added into the powders while stirring the powders with a rotating blade and the like under an inert gas atmosphere such as a nitrogen gas. The reason why the inert gas such as a nitrogen gas is used is to prevent decomposition of the treating agent from occurring. Thereafter, they are mixed under the same condition as the surface treatment by the second treating agent, which is then followed by cooling similarly to before.

By following the processes shown above, the surface-modified silica powder of the present invention can be produced. In the production method shown in this first embodiment of, each surface treatment by two surface treating agents is done in the separated processes; and thus, this production method is superior to the production method shown in the second embodiment of mentioned later because the silica powder having comparatively high fixing rates of the treating agents can be obtained in this method.

Production Method According to a Second Embodiment:

In the production method according to this second embodiment, prior to surface treatment of the silica powders, the first treating agent and the second treating agent are mixed to obtain a third treating agent; and then, surface treatment is carried out by only one time surface treatment by using this third treating agent. That is, in the third surface treating agent in this second embodiment, the first treating agent of the compound (A) and the second treating agent of the aminosilane (B) are mixed to form a covalent bond (amide bond) in advance by a condensation reaction of the carboxyl group or the carboxylic acid anhydride group (—CO—O—CO—) contained in the compound (A) with the amino group contained in the aminosilane (B).

Specifically, to begin with, the first treating agent of the compound (A) and the second treating agent of the aminosilane (B) are arranged. Usage amounts of the first treating agent of the compound (A) and the second treating agent of the aminosilane (B) are as same as those of the above-described first embodiment of the present invention.

The compound (A) and the aminosilane (B) arranged as mentioned above are diluted by or dissolved into an organic solvent to prepare the mixture solution of them. This mixture solution is stirred preferably at the temperature of 0 to 60° C. and with the time for 0.5 to 8 hours to facilitate a condensation reaction of the carboxyl group or the carboxylic acid anhydride group (—CO—O—CO—) contained in the compound (A) with the amino group contained in the aminosilane (B) thereby fully forming the third treating agent.

Then, the silica powders to be surface-modified are taken into a reactor; and then, the above-prepared mixture solution and water are added to the powders while stirring the powders with a rotating blade and the like under an inert gas atmosphere such as a nitrogen gas. The reason why the inert gas such as a nitrogen gas is used is to prevent decomposition of the treating agent from occurring. The reason why water is added is to form a silanol group by reacting the third treating agent with water. Amount of water to be added in this reaction is preferably in the range of 0.1 to 5 parts by mass relative to 100 parts by mass of the silica powders. Thereafter, this resulting mixture is mixed in the reactor at the temperature of 120 to 300° C. and with the time for 10 to 300 minutes. The reason why the temperature range of 120 to 300° C. is used is because below this lower limit the surface modification of the silica powders is insufficient so that sufficient effects by this surface treatment cannot be obtained. On the other hand, if it is above the upper limit, the surface treating agent decomposes in a certain instance; and thus, above this upper limit is not suitable. In this range, the treatment temperature is particularly preferably in the range of 150 to 250° C. In addition, if the mixing time is shorter than the lower limit, similarly to the case of the temperature, sufficient effects by this surface treatment cannot be obtained. On the other hand, if the time is longer than the upper limit, problems such as agglomeration of the powders and decomposition of the treating agent appear; or the reaction does not proceed further even if the mixing time is prolonged beyond the upper limit so that it is not suitable from the economical view point. In this range, the mixing time of 20 to 120 minutes is particularly preferable. After the treatment, the powders are cooled by cooling water, by allowing them to stand at room temperature, or by other methods.

By following the processes shown above, the surface-modified silica powder of the present invention can be produced. In the production method shown in this second embodiment, surface treatment by two surface treating agents is done by a single treatment; and thus, this production method is superior to the production method shown in the first embodiment mentioned above in productivity.

The surface-modified silica powder of the present invention obtained as mentioned above can be used suitably as an external additive to an electrophotographic toner; and the electrophotographic toner composition of the present invention contains this surface-modified silica powder as the external additive for it. Accordingly, it is not easily influenced by the use frequency and the use environment, thereby leading to drastic reduction of problems such as poor transcription and fouling of a machine during printing. The electrophotographic toner composition of the present invention is not particularly restricted except that the composition contains the surface-modified silica powder of the present invention as the external additive; and thus, the composition can be produced by using generally used various materials including a color pigment, a binder, a wax, and a charge controlling agent.

EXAMPLES

Next, Examples of the present invention, together with Comparative Examples, will be explained in detail.

Example 1

At first, γ-aminopropyl triethoxy silane was arranged as the second treating agent; and 10 g of this second treating agent was diluted by adding 10 g of ethanol as the organic solvent to prepare the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 200° C. under the nitrogen gas atmosphere for 120 minutes, and then, this was cooled by using cooling water.

Then, trimellitic anhydride 4-tert-butylphenol ester was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Example 1.

Example 2

At first, trimellitic anhydride 4-tert-butylphenol ester as the first treating agent and γ-aminopropyl triethoxy silane as the second treating agent were arranged. 60 g of methanol as the organic solvent was added to the thus arranged 13 g of the first treating agent and 10 g of the second treating agent to be dissolved in; and then, the resulting mixture was stirred at 60° C. for 8 hours to prepare the modifying solution.

Then, 100 g of fumed silica powders with the average primary particle diameter of 12 nm and the BET specific surface area of 200 $m^2/g$ obtained by a gas phase method (commercial name of AEROSIL (registered trade mark) 200, manufactured by Nippon Aerosil Co., Ltd.) was taken into a reactor; and then, into this reactor were added 1 g of water and the above-prepared modifying solution while stirring the powders by a rotating blade under the nitrogen gas atmosphere. The resulting mixture was mixed while stirring at 200° C. under the nitrogen gas atmosphere for 120 minutes, and then, this was cooled by cooling water to obtain the silica powders. The surface-modified silica powder obtained by this surface treatment was designated as Example 2.

Example 3

At first, γ-aminopropyl triethoxy silane was arranged as the second treating agent; and 10 g of this second treating agent was diluted by adding 10 g of ethanol as the organic solvent to obtain the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 200° C. under the nitrogen gas atmosphere for 120 minutes, and then, this was cooled by using cooling water.

Then, 4-tert-butylphthalic anhydride was arranged as the first treating agent; and 25 g of methanol as the organic solvent was added to 8 g of this first treating agent to obtain the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Example 3.

Example 4

At first, γ-aminopropyl triethoxy silane was arranged as the second treating agent; and 10 g of this second treating agent was diluted by adding 10 g of ethanol as the organic solvent to obtain the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 200° C. under the nitrogen gas atmosphere for 120 minutes, and then, this was cooled by using cooling water.

Then, 7 g of trimellitic anhydride 4-tert-butylphenol ester and 4 g of 4-tert-butylphthalic anhydride were arranged as the first treating agents; and then, 60 g of methanol as the organic solvent was added to the mixture to obtain the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Example 4.

Example 5

At first, N-(n-butyl)-3-aminopropyl trimethoxy silane was arranged as the second treating agent; and 11 g of this second treating agent was diluted by adding 11 g of ethanol as the organic solvent to prepare the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen atmosphere. The resulting mixture was mixed while stirring at 200° C. under the nitrogen atmosphere for 120 minutes, and then, this was cooled by using cooling water.

Then, trimellitic anhydride 4-tert-butylphenol ester was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Example 5.

Example 6

At first, γ-aminopropyl triethoxy silane was arranged as the second treating agent; and 10 g of this second treating agent was diluted by adding 10 g of ethanol as the organic solvent to prepare the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 200° C. under the nitrogen atmosphere for 120 minutes, and then, this was cooled by using cooling water.

Then, 4-tert-butylphthalic acid was arranged as the first treating agent; and 41 g of methanol as the organic solvent was added to 9 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by cooling water to obtain the silica powders. The surface-modified silica powder obtained by this surface treatment was designated as Example 6.

Example 7

At first, γ-aminopropyl triethoxy silane was arranged as the second treating agent; and 10 g of this second treating agent was diluted by adding 10 g of ethanol as the organic solvent to prepare the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen atmosphere. The resulting mixture was mixed while stirring at 200° C. under the nitrogen gas atmosphere for 120 minutes, and then, this was cooled by using cooling water.

Then, 4-(trifluoromethyl)salicylic acid was arranged as the first treating agent; and 37 g of methanol as the organic solvent was added to 8 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Example 7.

Example 8

At first, γ-aminopropyl triethoxy silane was arranged as the second treating agent; and 10 g of this second treating agent was diluted by adding 10 g of ethanol as the organic solvent to prepare the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 200° C. under the nitrogen atmosphere for 120 minutes, and then, this was cooled by using cooling water.

Then, 2,2-bis{(4-carboxyl)phenyl}glycolic acid was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Example 8.

Comparative Example 1

At first, 6 g of hexamethyl disilazane was arranged as the second treating agent. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and hexamethyl disilazane while stirring the powders by a rotating blade under the nitrogen atmosphere. The resulting mixture was mixed while stirring at 200° C. under the nitrogen atmosphere for 120 minutes, and then, this was cooled by using cooling water.

Then, trimellitic anhydride 4-tert-butylphenol ester was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Comparative Example 1.

Comparative Example 2

At first, 3-(dimethylamino) propyl trimethoxy silane was arranged as the second treating agent; and 9 g of this second treating agent was diluted by adding 9 g of ethanol as the organic solvent to prepare the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 200° C. under the nitrogen atmosphere for 120 minutes, and then, this was cooled by using cooling water.

Then, trimellitic anhydride 4-tert-butylphenol ester was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Comparative Example 2.

Comparative Example 3

At first, γ-aminopropyl triethoxy silane was arranged as the second treating agent; and 10 g of this second treating agent was diluted by adding 10 g of ethanol as the organic solvent to prepare the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 200° C. under the nitrogen atmosphere for 120 minutes, and then, this was cooled by using cooling water.

Then, trimellitic anhydride 4-tert-butylphenol ester was arranged as the first treating agent; and 10 g of methanol as the organic solvent was added to 1 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Comparative Example 3.

Comparative Example 4

At first, γ-aminopropyl triethoxy silane was arranged as the second treating agent; and 10 g of this second treating agent was diluted by adding 10 g of ethanol as the organic solvent to prepare the aminosilane solution. Then, 100 g of fumed silica powders with the average primary particle diameter of 12 nm and the BET specific surface area of 200 $m^2/g$ obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen atmosphere. The resulting mixture was mixed while stirring at 200° C. under the nitrogen atmosphere for 120 minutes, and then, this was cooled by using cooling water.

Then, trimellitic anhydride 4-tert-butylphenol ester was arranged as the first treating agent; and 110 g of methanol as the organic solvent was added to 24 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Comparative Example 4.

Comparative Example 5

At first, γ-aminopropyl triethoxy silane was arranged as the second treating agent; and 0.1 g of this second treating agent was diluted by adding 0.3 g of ethanol as the organic solvent to obtain the aminosilane solution. Then, 100 g of fumed silica powders with the average primary particle diameter of 12 nm and the BET specific surface area of 200 $m^2$/g obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 200° C. under the nitrogen gas atmosphere for 120 minutes, and then, this was cooled by using cooling water.

Then, trimellitic anhydride 4-tert-butylphenol ester was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Comparative Example 5.

Comparative Example 6

Into a reactor was taken 100 g of fumed silica powders with the average primary particle diameter of 12 nm and the BET specific surface area of 200 $m^2$/g obtained by a gas phase method (dry method) (commercial name of AEROSIL (registered trade mark) 200, manufactured by Nippon Aerosil Co., Ltd.); and then, 1 g of water and 21 g of γ-aminopropyl triethoxy silane as the second treating agent were added into this reactor while stirring the powders by a rotating blade under the nitrogen atmosphere. The resulting mixture was mixed while stirring at 200° C. under the nitrogen atmosphere for 120 minutes, and then, this was cooled by using cooling water.

Then, trimellitic anhydride 4-tert-butylphenol ester was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 200° C. for 120 minutes under the nitrogen atmosphere, it was again cooled by using cooling water to obtain the silica powders. The surface-modified silica powder obtained by this surface treatment was designated as Comparative Example 6.

Comparative Example 7

At first, γ-aminopropyl triethoxy silane was arranged as the second treating agent; and 10 g of this second treating agent was diluted by adding 10 g of ethanol as the organic solvent to prepare the aminosilane solution. Then, 100 g of fumed silica powders with the average primary particle diameter of 12 nm and the BET specific surface area of 200 $m^2$/g obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen atmosphere. The resulting mixture was mixed while stirring at 350° C. under the nitrogen atmosphere for 120 minutes, and then, this was cooled by using cooling water.

Then, trimellitic anhydride 4-tert-butylphenol ester was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 350° C. for 120 minutes under the nitrogen atmosphere, it was again cooled by using cooling water to obtain the silica powders. The surface-modified silica powder obtained by this surface treatment was designated as Comparative Example 7.

Comparative Example 8

At first, γ-aminopropyl triethoxy silane was arranged as the second treating agent; and 10 g of this second treating agent was diluted by adding 10 g of ethanol as the organic solvent to prepare the aminosilane solution. Then, 100 g of fumed silica powders with the average primary particle diameter of 12 nm and the BET specific surface area of 200 $m^2$/g obtained by a gas phase method (dry method) (commercial name of AEROSIL (registered trade mark) 200, manufactured by Nippon Aerosil Co., Ltd.) was taken into a reactor; and then, into this reactor were added 1 g of water and the above-prepared aminosilane solution while stirring the powders by a rotating blade under the nitrogen gas atmosphere. The resulting mixture was mixed while stirring at 80° C. under the nitrogen atmosphere for 120 minutes, and then, this was cooled by using cooling water.

Then, trimellitic anhydride 4-tert-butylphenol ester was arranged as the first treating agent; and 60 g of methanol as the organic solvent was added to 13 g of this first treating agent to prepare the dissolved solution.

Under the nitrogen atmosphere this dissolved solution was added into the reactor while stirring by a rotating blade the powders after treatment with the second treating agent. Then, after the resulting mixture was mixed by stirring at 80° C. for 120 minutes under the nitrogen atmosphere, it was again cooled by using cooling water to obtain the silica powders. The surface-modified silica powder obtained by this surface treatment was designated as Comparative Example 8.

TABLE 1

| | Silica powder | | | | Surface treatment | | | | | |
|---|---|---|---|---|---|---|---|---|---|---|
| | | | | | First modifying agent | | Second modifying agent | | | First modifying agent second modifying agent |
| | Kind | BET Specific surface area (m2/g) | Average primary particle diameter (nm) | Use amount (g) | Kind | Use amount (g) | Kind | Use amount (g) | Per 1 m2 (mg) | (molar ratio) |
| Example 1 | Fumed silica | 200 | 12 | 100 | Trimellitic anhydride 4-tert-butylphenol ester | 13 | γ-Aminopropyl trimethoxy silane | 10 | 0.5 | 0.9 |
| Example 2 | Fumed silica | 200 | 12 | 100 | Trimellitic anhydride 4-tert-butylphenol ester | 13 | γ-Aminopropyl trimethoxy silane | 10 | 0.5 | 0.9 |
| Example 3 | Fumed silica | 200 | 12 | 100 | 4-Tert-butylphthalic anhydride | | γ-Aminopropyl trimethoxy silane | 10 | 0.5 | 0.8 |
| Example 4 | Fumed silica | 200 | 12 | 100 | Trimellitic anhydride 4-tert-butyiphenol ester<br>4-Tert-butylphthalic anhydride | 7<br>4 | γ-Aminopropyl trimethoxy silane | 10 | 0.5 | 0.9 |
| Example 5 | Fumed silica | 200 | 12 | 100 | Trimellitic anhydride 4-tert-butylphenol ester | 13 | N-(n-Butyl)-3-aminopropyl trimethoxy silane | 11 | 0.6 | 0.9 |
| Example 6 | Fumed silica | 200 | 12 | 100 | 4-Tert-butylphthalic acid | 9 | γ-Aminopropyl trimethoxy silane | 10 | 0.5 | 0.9 |
| Example 7 | Fumed silica | 200 | 12 | 100 | 4-(Trifluoromethyl) salicylic acid | 8 | γ-Aminopropyl trimethoxy silane | 10 | 0.5 | 0.9 |
| Example 8 | Fumed silica | 200 | 12 | 100 | 2,2-Bis{(4-carboxyl) phenyl} glycolic acid | 13 | γ-Aminopropyl trimethoxy silane | 10 | 0.5 | 0.9 |
| Comparative Example 1 | Fumed silica | 200 | 12 | 100 | Trimellitic anhydride 4-tert-butylphenol ester | 13 | Hexamethyl disilazane | 6 | 0.3 | 1.1 |
| Comparative Example 2 | Fumed silica | 200 | 12 | 100 | Trimellitic anhydride 4-tert-butylphenol ester | 13 | 3-(Dimethylamino) propyl trimethoxy silane | 9 | 0.5 | 0.9 |
| Comparative Example 3 | Fumed silica | 200 | 12 | 100 | Trimellitic anhydride 4-tert-butylphenol ester | 1 | γ-Aminopropyl triethoxy silane | 10 | 0.5 | 0.1 |
| Comparative Example 4 | Fumed silica | 200 | 12 | 100 | Trimellitic anhydride 4-tert-butylphenol ester | 24 | γ-Aminopropyl triethoxy silane | 10 | 0.5 | 1.6 |
| Comparative Example 5 | Fumed silica | 200 | 12 | 100 | Trimellibc anhydride 4-tert-butylphenol ester | 13 | γ-Aminopropyl triethoxy silane | 0.1 | 0.005 | 88.8 |
| Comparative Example 6 | Fumed silica | 200 | 12 | 100 | Trimellitic anhydride 4-tert-butylphenol ester | 13 | γ-Aminopropyl triethoxy silane | 21 | 1.05 | 0.4 |
| Comparative Example 7 | Fumed silica | 200 | 12 | 100 | Trimellitic anhydride 4-tert-butylphenol ester | 13 | γ-Aminopropyl triethoxy silane | 10 | 0.5 | 0.9 |
| Comparative Example 8 | Fumed silica | 200 | 12 | 100 | Trimellitic anhydride 4-tert-butylphenol ester | 13 | γ-Aminopropyl triethoxy silane | 10 | 0.5 | 0.9 |

Comparative Tests and Evaluation

The fixing rate, the hydrophobic rate, and the triboelectrostatic charge amount of the surface-modified silica powder of each of Examples 1 to 8 and Comparative Examples 1 to 8 were evaluated. These results are shown in Table 2.

(1) Fixing Rate:

At first, carbon amount present in the respective powders after the surface treatment was measured by the elemental analysis instrument Sumigraph NC-22F (manufactured by Sumika Chemical Analysis Service, Ltd.) in advance. Then, by using a Soxhlet extractor (manufactured by BUCHI Labortechnik AG), 0.7 g sample of the respective powders was placed in a cylindrical filtration paper having a diameter of 28 mm; and then, releasable treating agents on the powders were extracted by using methanol as the extraction solvent with the extraction time of 60 minutes and the rinsing time of 30 minutes. Carbon amount of the powders after removal of the releasable treating agents by extraction was measured by using the foregoing elemental analysis instrument. Percentage of the carbon amount in the powders after the extraction relative to the carbon amount in the powders before the extraction (carbon amount in powders after extraction/carbon amount in powders before extraction×100) was calculated; and this value was taken as the fixing rate.

(2) Hydrophobic Rate:

The powders (1 g) after the surface treatment were weighed into a 200-mL separating funnel and 100 mL of pure water was added to the powders; and then, after the funnel was stoppled, the resulting mixture solution was shaken by using a turbula mixer with the rotation speed of 90 rpm for 10 minutes. After shaking, the mixture was settled for 10 minutes. After the settlement, 20 to 30 mL of the lower layer in the mixture solution was withdrawn from the funnel; and then, the withdrawn solution was taken into a 10-mm quartz cell to measure the light transmittance at the wavelength of 500 nm by a colorimeter by using pure water as the blank solution. This transmittance was taken as the hydrophobic rate.

(3) Triboelectrostatic Charge Amount:

At first, 50 g of a ferrite carrier and 0.1 g of the surface-modified silica powders obtained were taken into a glass vessel (75 mL). After the vessel was stoppled, it was shaken by using a turbler mixer with the rotation speed of 90 rpm for 5 minutes; and then, 0.1 g of the ferrite carrier mixed with the silica powders was taken. This was blown by a nitrogen gas for 1 minute by using the blow-off charge amount measurement instrument TB-200 Type (manufactured by KYOCERA Chemical Corp.); and then, the charge amount thus obtained was taken as the triboelectrostatic charge amount.

TABLE 2

| | Fixing rate (%) | Hydrophobic rate (%) | Triboelectrostatic charge amount (μC/g) |
|---|---|---|---|
| Example 1 | 99 | 100 | −90 |
| Example 2 | 98 | 91 | −110 |
| Example 3 | 94 | 100 | +20 |
| Example 4 | 99 | 97 | −30 |
| Example 5 | 99 | 95 | −150 |
| Example 6 | 93 | 100 | +20 |
| Example 7 | 91 | 99 | +25 |
| Example 8 | 90 | 99 | −40 |
| Comparative Example 1 | 99 | 33 | −400 |
| Comparative Example 2 | 0 | 31 | +50 |
| Comparative Example 3 | 33 | 100 | +100 |
| Comparative Example 4 | 99 | 28 | −50 |
| Comparative Example 5 | 56 | 19 | −270 |
| Comparative Example 6 | 40 | 45 | +210 |
| Comparative Example 7 | 0 | 0 | −70 |
| Comparative Example 8 | 0 | 5 | −90 |

As can be seen in Table 2, the surface-modified silica powder of Examples 1 to 8 has a high fixing rate and a high hydrophobic rate concurrently when it is added to a toner as the external additive. Because of this, these powders have excellent temporal stability of the triboelectrostatic charge amount; and in addition, they can keep stable triboelectrostatic charge amount when they are used under not only a low temperature and low humidity environment but also a high temperature and high humidity environment. Further, because the triboelectrostatic charge amount thereof is 200 μC/g or less in its absolute value, excessively high triboelectrostatic charge amount of the toner can be suppressed. Accordingly, problems such as fogging and decrease in image quality during printing can be significantly reduced.

INDUSTRIAL APPLICABILITY

The surface-modified silica powder of the present invention can be used as an external additive to improve fluidity, control conductivity, or enhance transcription property and durability of a toner, in such a use as a toner for an electrophotographic developer.

The invention claimed is:

1. A surface-modified silica powder, characterized in that the surface of the silica powder is treated by using:

one or two or more of a compound (A) shown by any one of the following general formulae (1) to (4) as a first treating agent, and an aminosilane (B) as a second treating agent, respectively, wherein a fixing rate of the compound (A) and the aminosilane (B) is a total of 50% or more, a hydrophobic rate is 80% or more, and a triboelectrostatic charge amount is 200 μC/g or less in its absolute value,

[Chem. 1]

(1)

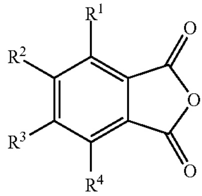

wherein R' to $R^4$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^1$ and $R^2$, $R^2$ and $R^3$, and $R^3$ and $R^4$ may be bonded with each other to form a ring by a single bond or via an optionally substituted methylene group, an oxygen atom, or a sulfur atom,

[Chem. 2]

(2)

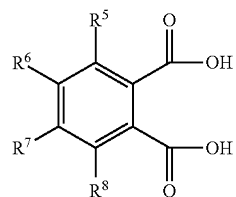

wherein $R^5$ to $R^8$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^5$ and $R^6$, $R^6$ and $R^7$, and $R^7$ and $R^8$ may be bonded with each other to form a ring by a single bond or via an optionally substituted methylene group, an oxygen atom, or a sulfur atom,

[Chem. 3]

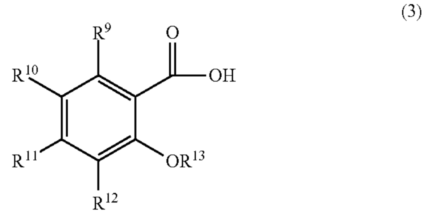

wherein $R^9$ to $R^{12}$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^9$ and $R^{10}$, $R^{10}$ and $R^{11}$, and $R^{11}$ and $R^{12}$ may be bonded with each other to form a ring by a single bond or via an optionally substituted methylene group, an oxygen atom, or a sulfur atom. $R^{13}$ represents a hydrogen atom, a deuterium atom, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted aromatic hydrocarbon group, an optionally substituted heterocyclic group, an optionally substituted condensed polycyclic aromatic group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group,

[Chem. 4]

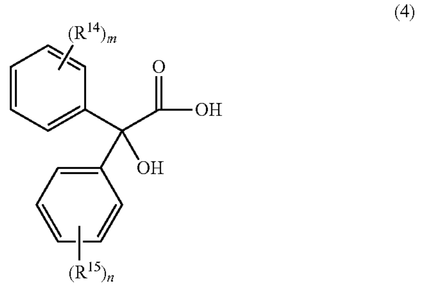

wherein $R^{14}$ and $R^{15}$ may be the same or different with each other while representing a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group, wherein these groups may be bonded with each other to form a ring. Reference characters "m" and "n" may be the same or different with each other while representing zero or an integer of 1 to 4.

2. The surface-modified silica powder according to claim 1, characterized in that the silica powder is a fumed silica.

3. The surface-modified silica powder according to claim 1, characterized in that the first treating agent is one or two or more of a compound (A) shown by the general formula (1) or (2), and the second treating agent is a primary aminosilane or a secondary aminosilane.

4. The surface-modified silica powder according to claim 1, characterized in that the first treating agent is one or two or more of a compound (A) shown by the general formula (1) or (2), wherein $R^1$ to $R^4$ in the general formula (1) represent a branched alkyl group having 4 to 6 carbon atoms or an optionally substituted aryl oxycarbonyl group, and $R^5$ to $R^8$ in the general formula (2) represent a branched alkyl group having 4 to 6 carbon atoms or an optionally substituted aryl oxycarbonyl group.

5. The surface-modified silica powder according to claim 1, characterized in that a molar ratio of the first treating agent to the second treating agent (first treating agent/second treating agent) used in the surface treatment is in the range of 0.2 to 1.5, and amount of the second treating agent used for the silica powder is in the range of 0.01 to 1.0 mg per 1 $m^2$ of the silica powder surface area.

6. A method for producing a silica powder whose surface is modified by surface treatment of a silica powder, characterized in that the said surface treatment is done by using a first treating agent and a second treating agent, wherein the first treating agent is one or two or more of a compound (A) shown by any one of the following general formulae (1) to (4), and the second treating agent is an aminosilane (B),

[Chem. 5]

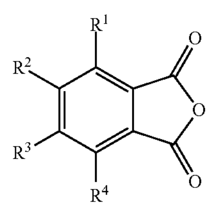

wherein $R^1$ to $R^4$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^1$ and $R^2$, $R^2$ and $R^3$, and $R^3$ and $R^4$ may be bonded with each other to form a ring by a single bond or via an optionally substituted methylene group, an oxygen atom, or a sulfur atom,

[Chem. 6]

(2)

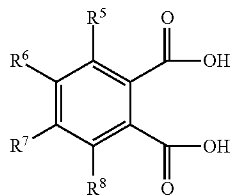

wherein $R^5$ to $R^8$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^5$ and $R^6$, $R^6$ and $R^7$, and $R^7$ and $R^8$ may be bonded with each other to form a ring by a single bond or via an optionally substituted methylene group, an oxygen atom, or a sulfur atom,

[Chem. 7]

(3)

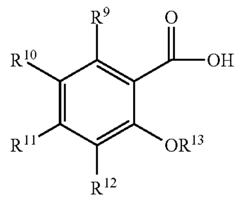

wherein $R^9$ to $R^{12}$ may be the same or different with each other while representing a hydrogen atom, a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group. $R^9$ and $R^{10}$, $R^{10}$ and $R^{11}$, and $R^{11}$ and $R^{12}$ may be bonded with each other to form a ring by a single bond or via an optionally substituted methylene group, an oxygen atom, or a sulfur atom. $R^{13}$ represents a hydrogen atom, a deuterium atom, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted aromatic hydrocarbon group, an optionally substituted heterocyclic group, an optionally substituted condensed polycyclic aromatic group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group,

[Chem. 8]

(4)

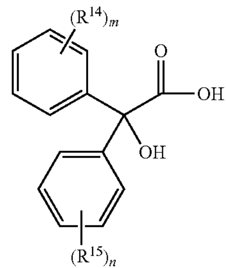

wherein $R^{14}$ and $R^{15}$ may be the same or different with each other while representing a deuterium atom, a fluorine atom, a chlorine atom, a hydroxyl group, a cyano group, a nitro group, a carboxyl group, an optionally substituted liner or branched alkyl group having 1 to 6 carbon atoms, an optionally substituted cycloalkyl group having 5 to 10 carbon atoms, an optionally substituted linear or branched alkenyl group having 2 to 6 carbon atoms, an optionally substituted linear or branched alkyloxy group having 1 to 6 carbon atoms, an optionally substituted cycloalkyloxy group having 5 to 10 carbon atoms, an optionally substituted aromatic hydrocarbon group, an optionally substituted heterocyclic group, an optionally substituted condensed polycyclic aromatic group, an optionally substituted aryloxy group, an optionally substituted liner or branched alkyl oxycarbonyl group having 1 to 6 carbon atoms, an optionally substituted aryl oxycarbonyl group, an optionally substituted liner or branched aliphatic acyl group having 1 to 8 carbon atoms, or an optionally substituted aromatic acyl group, wherein these groups may be bonded with each other to form a ring. Reference characters "m" and "n" may be the same or different with each other while representing zero or an integer of 1 to 4.

7. The method for producing a surface-modified silica powder according to claim 6, characterized in that the second treating agent is added to and mixed with the silica powder, the resulting mixture is treated at the temperature of 120 to 300° C. and with the time for 10 to 300 minutes under an inert gas atmosphere, the first treating agent is added to and mixed with the silica powder having been treated with the second treating agent, and then, this mixture is treated at the temperature of 120 to 300° C. and with the time for 10 to 300 minutes under an inert gas atmosphere.

8. The method for producing a surface-modified silica powder according to claim 6, characterized in that after a third treating agent is prepared by mixing the first treating agent and the second treating agent, the said third treating agent is added to and mixed with the silica powder, and then, surface treatment thereof is carried out at the temperature of 120 to 300° C. and with the time for 10 to 300 minutes under an inert gas atmosphere.

9. The method for producing a surface-modified silica powder according to claim 6, characterized in that a molar ratio of the first treating agent to the second treating agent (first treating agent/second treating agent) used in the surface treatment is in the range of 0.2 to 1.5, and amount of the second treating agent used for the silica powder is in the range of 0.01 to 1.0 mg per 1 $m^2$ of the silica powder surface area.

10. A toner external additive comprising the surface-modified silica powder according to claim 1.

11. An electrophotographic toner composition containing the toner external additive according to claim 10.

* * * * *